(12) United States Patent
Bockenstedt et al.

(10) Patent No.: US 12,114,908 B2
(45) Date of Patent: Oct. 15, 2024

(54) METHODS AND APPARATUS FOR PUMPING COOLANT TO AN ENERGY DELIVERY DEVICE

(71) Applicant: Solta Medical Ireland Limited, Dublin (IE)

(72) Inventors: Craig Robert Bockenstedt, Bothell, WA (US); Gregory T. Wing, Carnation, WA (US)

(73) Assignee: Solta Medical Ireland Limited, Dublin (IE)

( * ) Notice: Subject to any disclaimer, the term of this patent is extended or adjusted under 35 U.S.C. 154(b) by 179 days.

(21) Appl. No.: 17/835,057

(22) Filed: Jun. 8, 2022

(65) Prior Publication Data

US 2022/0409256 A1  Dec. 29, 2022

Related U.S. Application Data (63) Continuation of application No. 16/556,616, filed on Aug. 30, 2019, now Pat. No. 11,395,692.

(60) Provisional application No. 62/725,562, filed on Aug. 31, 2018.

(51) Int. Cl.
  *A61B 18/02* (2006.01)
  *A61B 18/12* (2006.01)
  *A61B 18/18* (2006.01)
  *A61B 18/00* (2006.01)

(52) U.S. Cl.
  CPC .......... *A61B 18/02* (2013.01); *A61B 18/1206* (2013.01); *A61B 18/18* (2013.01); *A61B 2018/00452* (2013.01); *A61B 2018/00642* (2013.01); *A61B 2018/00791* (2013.01); *A61B 2018/1253* (2013.01); *A61B 2018/126* (2013.01); *A61B 2018/1266* (2013.01); *A61B 2018/128* (2013.01)

(58) Field of Classification Search
  CPC . A61B 18/02; A61B 18/0218; A61B 18/1206; A61B 18/1402; A61B 18/18; A61B 2018/00029; A61B 2018/00452; A61B 2018/00458; A61B 2018/00642; A61B 2018/00791; A61B 2018/00797; A61B 2018/1253; A61B 2018/126; A61B 2018/1266; A61B 2018/128; A61B 2090/064; A61N 1/06; A61N 1/328; A61N 1/403
  See application file for complete search history.

(56) References Cited

U.S. PATENT DOCUMENTS

| | | | |
|---|---|---|---|
| 6,413,255 B1 * | 7/2002 | Stern | A61N 5/04 606/41 |
| 6,905,496 B1 * | 6/2005 | Ellman | A61B 18/0218 606/41 |
| 7,006,874 B2 | 2/2006 | Knowlton et al. | |
| 7,476,242 B2 * | 1/2009 | Matlock | A61B 18/1485 607/104 |
| 7,481,809 B2 * | 1/2009 | Stern | A61N 1/06 606/41 |
| 8,515,553 B2 * | 8/2013 | Schenck | A61B 18/14 607/102 |

* cited by examiner

*Primary Examiner* — Michael F Peffley
(74) *Attorney, Agent, or Firm* — Thompson Hine LLP (57) ABSTRACT

Apparatus and methods for delivering coolant to an energy delivery device used to treat tissue with electromagnetic energy. A cooling system includes a pump that is configured to pump a coolant to the energy delivery device.

19 Claims, 6 Drawing Sheets

METHODS AND APPARATUS FOR PUMPING COOLANT TO AN ENERGY DELIVERY DEVICE

CROSS-REFERENCE TO RELATED APPLICATIONS

This application is a continuation of application Ser. No. 16/556,616, filed Aug. 30, 2019 (now U.S. Pat. No. 11,395,692), which claims the benefit of U.S. Provisional Application No. 62/725,562, filed Aug. 31, 2018, which are fully incorporated by reference herein in their entirety.

FIELD OF THE INVENTION

The invention generally relates to apparatus and methods for delivering coolant to an energy delivery device used to treat tissue with electromagnetic energy.

BACKGROUND

Certain types of energy delivery devices are capable of treating a patient's tissue with electromagnetic energy. These energy delivery devices, which emit electromagnetic energy in different regions of the electromagnetic spectrum for tissue treatment, may be used to treat a multitude of diverse skin conditions. For example, the energy delivery device may non-ablatively and non-invasively treat a skin condition or other type of tissue condition.

One variety of these energy delivery devices emits high frequency electromagnetic energy in the radio-frequency (RF) band of the electromagnetic spectrum. The high frequency energy may be used to treat skin tissue by passing high frequency energy through a surface of the skin, while actively cooling the skin to prevent damage to the skin's epidermal layer closer to the skin surface. The high frequency energy heats tissue beneath the epidermis to a temperature sufficient to denature collagen, which causes the collagen to contract and shrink and, thereby, tighten the tissue. Treatment with high frequency energy also causes a mild inflammation. The inflammatory response of the tissue causes new collagen to be generated over time (between three days and six months following treatment), which results in further tissue contraction.

Typically, energy delivery devices include a treatment tip that is placed in contact with, or proximate to, the patient's skin surface and that emits electromagnetic energy that penetrates through the skin surface and into the tissue beneath the skin surface. The non-patient side of the energy delivery device, such as an electrode for high frequency energy, in the treatment tip may be sprayed with a coolant or cryogen spray. Heat is conducted from the warmer tissue to the cooler treatment tip, which cools tissue to a shallow depth beneath the skin surface. A controller may trigger the coolant spray based upon an evaluation of the temperature readings received as feedback from temperature sensors in the treatment tip.

The cryogen spray may be used to pre-cool superficial tissue before delivering the electromagnetic energy. When the electromagnetic energy is delivered, the superficial tissue that has been cooled is protected from thermal effects. The target tissue that has not been cooled or that has received nominal cooling will warm up to therapeutic temperatures resulting in the desired therapeutic effect. The amount or duration of pre-cooling can be used to select the depth of the protected zone of untreated superficial tissue. After the delivery of electromagnetic energy has concluded, the cryogen spray may also be employed to prevent or reduce heat originating from treated tissue from conducting upward and heating the more superficial tissue that was cooled before treatment with the electromagnetic energy.

Previous devices used, and relied upon, a heated reservoir to provide pressurized cryogen. A heated reservoir may require a large amount of time to startup or recover after replacing a spent cryogen canister. Indeed, users are often forced to wait several minutes while the cryogen system is pressurized when the system is powered on or after a fresh canister of cryogen is installed.

Although conventional methods and apparatus for delivering cryogen sprays have proved adequate for their intended purpose, what is needed are improved methods and apparatus for delivering a coolant, such as a cryogen, to the treatment tip.

SUMMARY

In an embodiment, a method for treating tissue beneath a skin surface with electromagnetic energy includes pumping a fluid from a container to an energy delivery device configured to emit the electromagnetic energy.

In an embodiment, an apparatus for treating tissue beneath a skin surface with electromagnetic energy includes an energy delivery device configured to deliver the electromagnetic energy to the tissue and a cooling system with a pump configured to pump a coolant or cryogen to the energy delivery device.

BRIEF DESCRIPTION OF THE DRAWINGS

The accompanying drawings, which are incorporated in and constitute a part of this specification and in which like reference numerals refer to like features, illustrate embodiments of the invention and, together with a general description of the invention given above and the detailed description of the embodiments given below, serve to explain the principles of the invention.

DETAILED DESCRIPTION

Referring now to the drawings, FIGS. 1-5 describe a treatment apparatus 10 that generally includes a handpiece 12, a treatment tip 14 that may be coupled in a removable and releasable manner with the handpiece 12, a console generally indicated by reference numeral 16, and a system controller 18. The system controller 18, which is incorporated into the console 16, orchestrates the global operation of the different individual components of the treatment apparatus 10. Under the control of the system controller 18 and any operator interaction with the system controller 18 at the console 16 and with controls at the handpiece 12, the treatment apparatus 10 is adapted to deliver electromagnetic energy in a high frequency band of the electromagnetic spectrum to a region of a patient's tissue. The electromagnetic energy, which may be delivered non-invasively and non-ablatively, heats the tissue to a targeted temperature range. The elevation in temperature may produce for example, changes in collagen fibers that achieve a desired treatment result, such as removing or reducing wrinkles and otherwise tightening the skin to thereby improve the appearance of a patient 20 receiving the treatment.

The treatment tip 14 may provide, either alone or in combination with the handpiece 12, an energy delivery member that includes a treatment electrode 24. In a representative embodiment, the treatment electrode 24 may be arranged on a flexible circuit that includes an electrically-insulating substrate 30 composed of a non-conductive dielectric material and a region 28 composed of an electrical conductor carried on the electrically-insulating substrate 30. The electrically-insulating substrate 30 may include a contact side 32 that is placed in contact with the skin surface and a non-contact side 34 that is opposite from the contact side 32. The conductor region 28 of the treatment electrode 24 is physically carried on the non-contact side 34 of the substrate 30 and is therefore separated by the substrate 30 from the skin surface during treatment.

Figure 4:
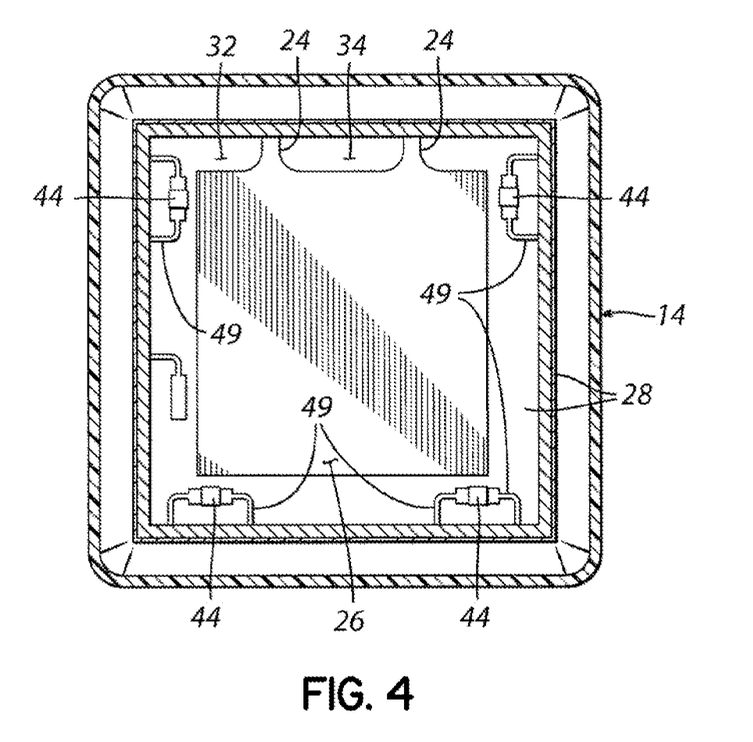
FIG. 4 is a rear view of an assembled treatment tip showing an electrode and temperature sensors.
Figure 5:
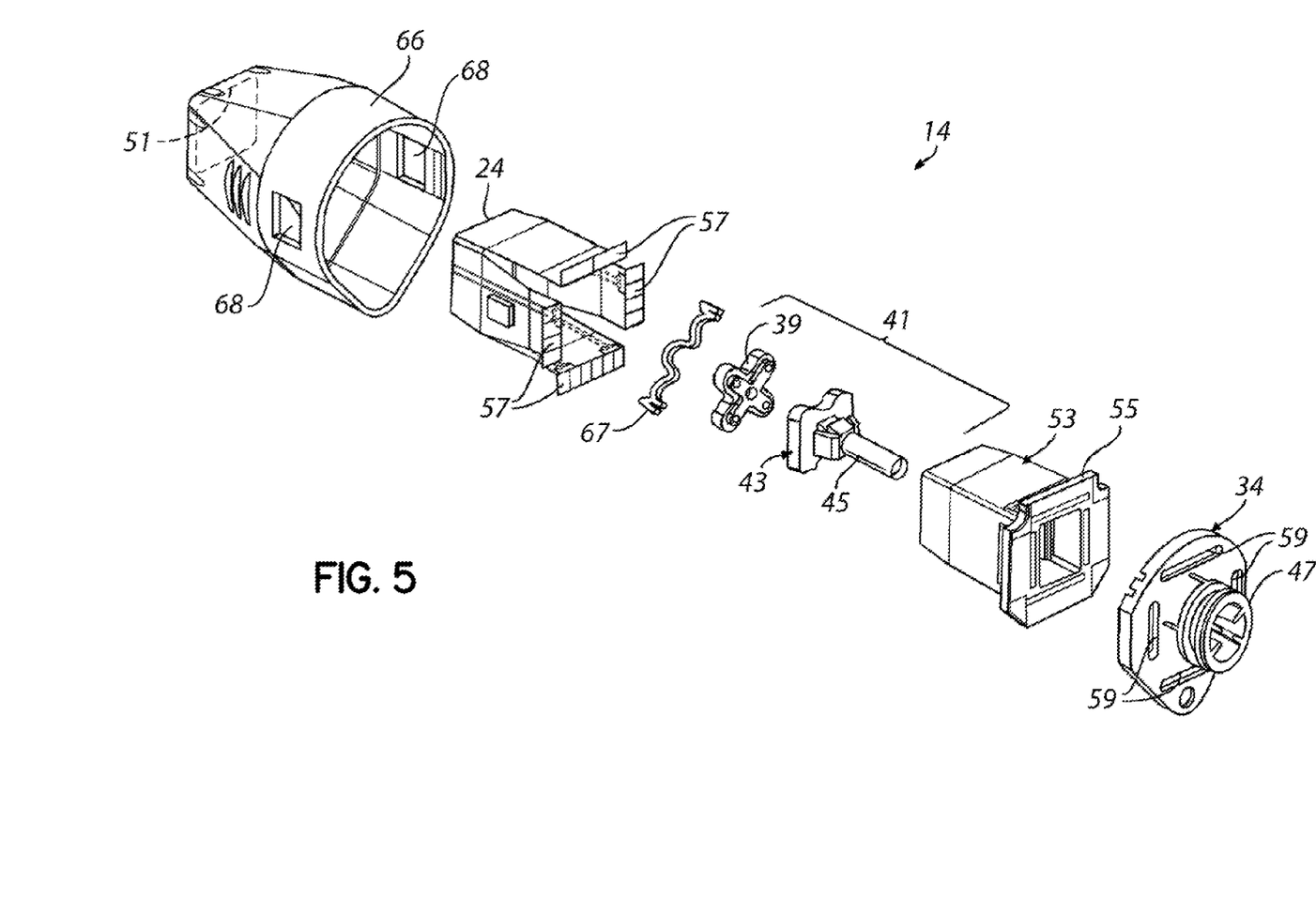
FIG. 5 is an exploded view of the treatment tip of FIG. 4 in which the treatment electrode is shown in an unfolded condition.

The substrate 30 of the flexible circuit may include a thin flexible base polymer film with thin conductive leads or traces 49. Some of the leads 49 may electrically couple the conductor region 28 with one or more contact pads 57. The base polymer film of substrate 30 may be, for example, polyimide or another material with a relatively high electrical resistivity and a relatively high thermal conductivity. The traces 49 and contact pads 57 may contain copper or another conductor characterized by a relatively high electrical conductivity. The traces 49 and contact pads 57 may be formed by depositing a layer of the conductor on the substrate 30 and patterning the conductor layer with lithography and etching processes. Instead of the representative single conductor region 28, the conductor region 28 may be segmented into plural individual electrodes that can be individually powered to sequentially deliver electromagnetic energy to the tissue.

Figure 1:
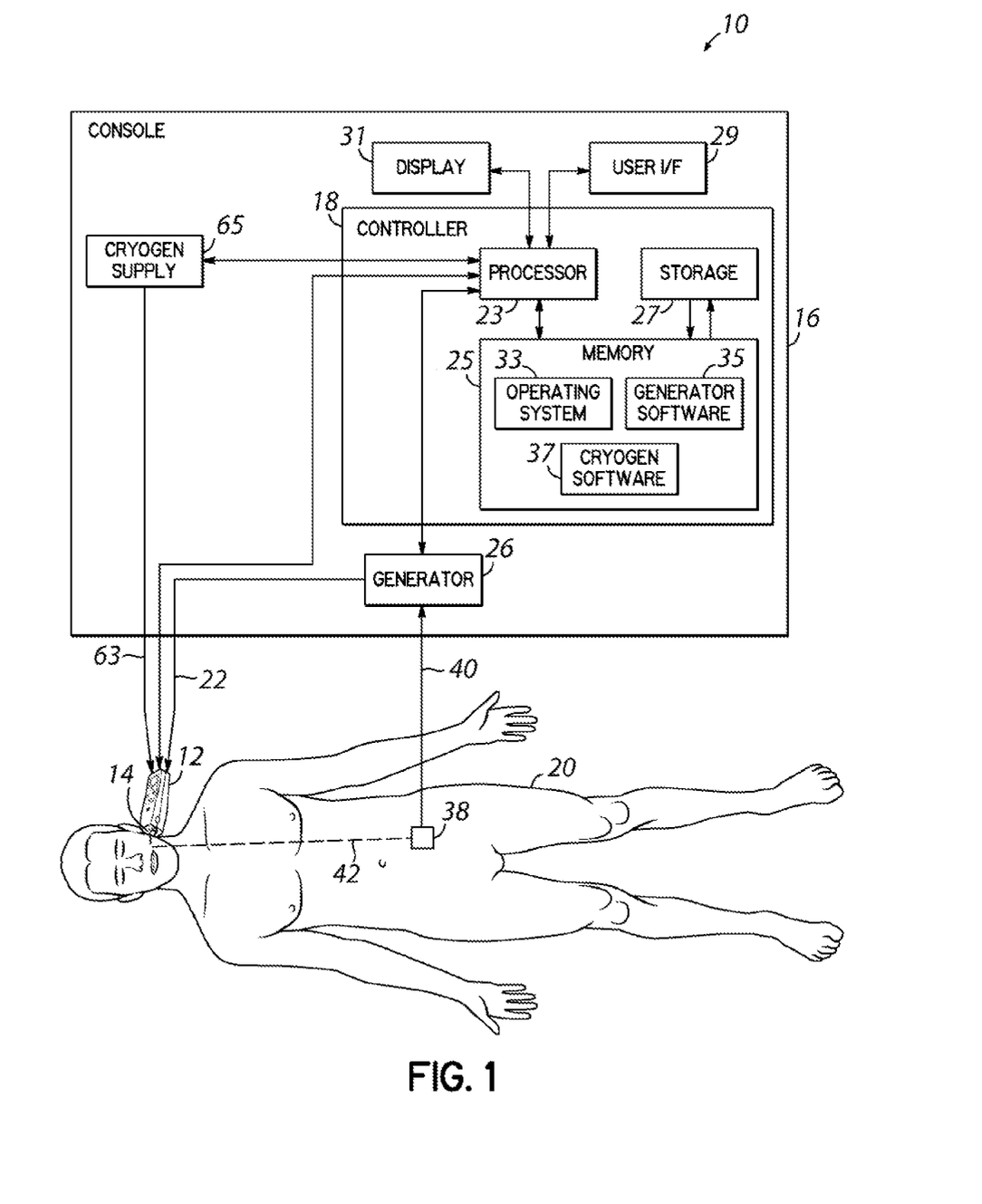
FIG. 1 is a diagrammatic view of a treatment system with a handpiece, a treatment tip, a console, and a generator.

The treatment electrode 24 is electrically coupled through the traces 49 and contact pads 57 by a set of insulated and shielded conductors 22 that extend from the handpiece 12 to the generator 26 at the console 16. The generator 26 is configured to generate the electromagnetic energy used in the treatment to impart a therapeutic effect by heating target tissue beneath the patient's skin surface. The generator 26, which may have the form of a high frequency power supply, is equipped with an electrical circuit operative to generate high frequency electrical current, typically in the radio-frequency (RF) band of the electromagnetic spectrum. The electrical circuit in the generator 26 converts a line alternating current voltage into drive signals for the treatment electrode 24. The drive signals have parameters (e.g., energy content and duty cycle) appropriate for the amount of power and the mode of operation that have been selected by the treating clinician. In alternative embodiments, the treatment apparatus 10 may be configured to deliver energy in the infrared band, microwave band, or another high frequency band of the electromagnetic spectrum, rather than within the RF band, to the patient's tissue.

The system controller 18 include at least one processor 23 coupled to a memory 25. The at least one processor 23 may represent one or more microprocessors, and the memory 25 may represent the random access memory (RAM) comprising the main storage of system controller 18, as well as any supplemental levels of memory, e.g., cache memories, non-volatile or backup memories (e.g., programmable or flash memories), read-only memories, etc. In addition, memory 25 may be considered to include memory storage physically located elsewhere in system controller 18, e.g., any cache memory in a processor 23, as well as any storage capacity used as a virtual memory, e.g., as stored on a mass storage device 27 or another computer (not shown) coupled to system controller 18 via a network.

System controller 18 also typically receives a number of inputs and outputs for communicating information externally. For interface with a user or operator, system controller 18 typically includes one or more user input devices (e.g., a keyboard, a mouse, a trackball, a joystick, a touchpad, a keypad, a stylus, and/or a microphone, among others) in the form of a user interface 29. The user interface 29 may be used to deliver instructions to the system controller 18 to adjust the generator 26 and to establish treatment settings based upon operator input at the handpiece 12. System controller 18 may also include a display 31 (e.g., a CRT monitor or an LCD display panel, among others).

System controller 18 operates under the control of an operating system 33, and executes or otherwise relies upon various computer software applications, components, programs, objects, modules, data structures, etc. In general, the routines executed by the system controller 18 to operate the treatment apparatus 10, whether implemented as part of an operating system or a specific application, component, program, object, module or sequence of instructions, will be referred to herein as "computer program code." The computer program code typically comprises one or more instructions that are resident at various times in various non-transitory memory and storage devices in a computer, and that, when read and executed by one or more processors in a computer, causes that computer to perform the steps necessary to execute steps or elements embodying the various aspects of the operation of the treatment apparatus 10.

The system controller 18 includes digital and/or analog circuitry that interfaces the processor 23 with the generator 26 for regulating the power delivered from the generator 26 to the treatment electrode 24. Generator software 35 resides as an application (i.e., program code) in the memory 25 and is executed by the processor 23 in order to issue commands that control the operation of the generator 26. The system controller 18 includes digital and/or analog circuitry that interfaces the processor 23 with a cryogen supply 65, described more fully below, for regulating the cryogen delivered to the treatment electrode 24. Cryogen software 37 resides as an application (i.e., program code) in the memory 25 and is executed by the processor 23 in order to issue commands that control the operation of the cryogen supply 65.

During a tissue treatment involving the treatment electrode 24, the substrate 30 is arranged between the conductor region 28 and the skin surface of the patient. Electromagnetic energy may be transmitted in a transcutaneous manner from the conductor region 28 through the thickness of substrate 30 and across the surface area of the portion to the tissue by capacitively coupling with the tissue of the patient 20.

As best shown in FIG. 4, the treatment tip 14 includes temperature sensors 44, such as thermistors, that are located on the non-contact side 34 of the substrate 30 that is not in contact with the patient's skin surface. Typically, the temperature sensors 44 are arranged about the perimeter of the conductor region 28 of the treatment electrode 24. Temperature sensors 44 are constructed to detect the temperature of the treatment electrode 24 and/or treatment tip 14, which may be representative of the temperature of the treated tissue. The temperature sensors 44 are electrically coupled by the conductive traces 49 with the contact pads 57, which are used to supply direct current (DC) voltages from the system controller 18 through the electrical wiring to the temperature sensors 44. The measured temperature reflects the temperature of the treated tissue and may be used as feedback in a control loop controlling energy delivery and/or cooling of the skin surface. The treatment tip 14 may also include pressure sensors (not shown) for detecting physical contact between the treatment electrode 24 and the skin surface of the patient 20.

Figure 2:
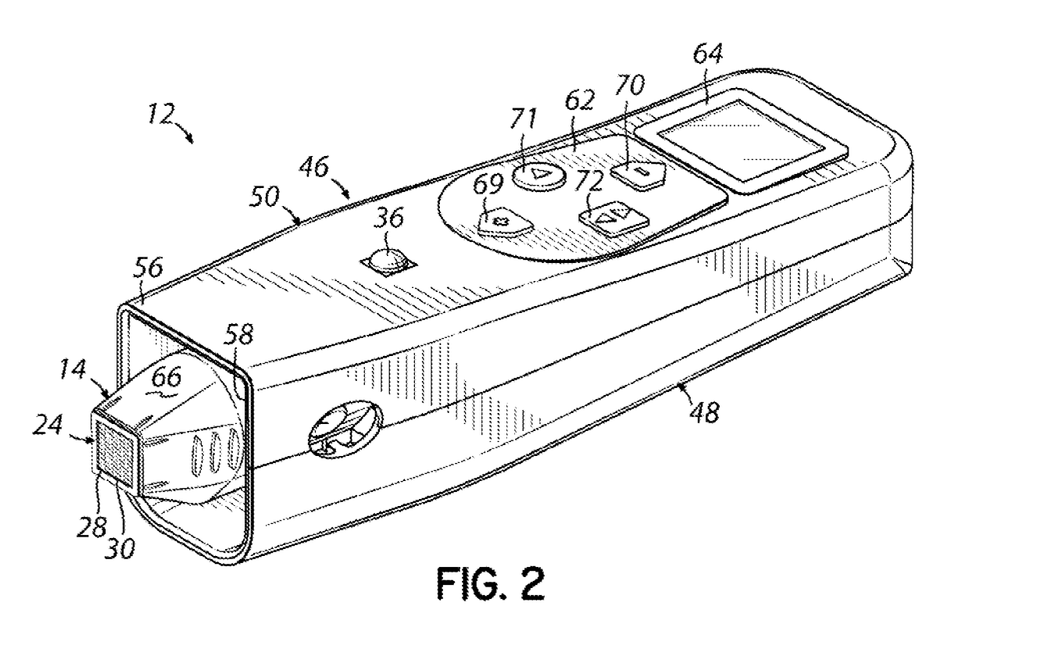
FIG. 2 is a perspective view of an assembly consisting of an embodiment of the handpiece and treatment tip for use with the treatment system of FIG. 1.

An activation button 36, which is accessible to the operator from the exterior of the handpiece 12, is configured to be actuated to close a switch in a normally open circuit with the generator 26. The closed circuit energizes the treatment electrode 24. Actuation of the activation button 36 triggers delivery of the high frequency energy over a short timed delivery cycle to the target tissue. After a fixed amount of time has elapsed, the delivery of high frequency energy from the treatment electrode 24 to the tissue at the treatment site is discontinued. In a stamping mode of operation, the handpiece 12 is manipulated to position the treatment tip 14 near a different treatment site on the skin surface and another cycle of high frequency energy is delivered to the patient's tissue. This process may be repeated for an arbitrary number of treatment sites.

High frequency electrical current flowing between the treatment electrode 24 and the patient 20 is concentrated at the skin surface and the underlying tissue across the contacting surface area of the portion of the treatment electrode 24. Capacitive coupling of the high frequency electromagnetic energy relies on energy transfer from the conductor region 28 through the dielectric material of the substrate 30 to create an electric field across the surface area where the treatment electrode 24 contacts the patient's body. The time-varying electric field induces electrical currents within the surrounding tissue beneath the skin surface.

Because of the natural resistance of tissue to electrical current flow, volumetric heating results within the tissue. The volumetric heating delivers a therapeutic effect to the tissue near the treatment site. For example, heating to a temperature of 50° C. or higher may contract collagen, which may result in tissue tightening or another aesthetic effect to improve the patient's appearance. The heating depth in the tissue is based upon the size and geometry of the treatment electrode 24 and, contingent upon the selection and configuration of the treatment tip 14, can be controlled to extend from a few hundred micrometers beneath the skin surface to several millimeters.

A non-therapeutic passive return electrode 38 is used to electrically couple the patient 20 with the generator 26. During patient treatment, the high frequency current flows from the treatment electrode 24 through the treated tissue and the intervening bulk of the patient 20 to the return electrode 38 and then to the generator 26 through conductors inside a return cable 40 to define a closed circuit or current path 42. The return electrode 38 is physically attached by, for example, an adhesive bond to a site on the body surface of the patient 20, such as the patient's back.

The surface area of the return electrode 38 in contact with the patient 20 may be relatively large in comparison with the surface area of the treatment electrode 24. Consequently, at the tissue adjacent to the return electrode 38, the current density flowing from the patient 20 to the return electrode 38 is relatively low in comparison with the current density flowing from the treatment electrode 24 to the patient 20. Because negligible heating is produced at its attachment site to the patient, a non-therapeutic effect is created in the tissue adjacent to the return electrode 38.

Although the treatment electrode 24 and the return electrode 38 are representatively configured for the delivery of monopolar high frequency energy, the treatment electrode 24 may be configured to deliver bipolar high frequency energy. The modifications to the treatment apparatus 10 required to deliver bipolar high frequency energy are familiar to a person having ordinary skill in the art. For example, the return electrode 38 may be eliminated from the treatment apparatus 10 and a bipolar type of treatment electrode substituted for the monopolar treatment electrode 24.

With continued reference to FIGS. 1-5, the handpiece 12 is constructed from a housing 46 that includes a body 48, a cover 50 assembled by conventional fasteners with the body 48, and an electrical/fluid interface 52 for the treatment tip 14. The housing 46 may be fabricated by an injection molding process using a suitable polymer resin as a construction material. The body 48 and cover 50 constitute shell halves that are integrally fastened together as an assembly. The housing 46 encloses an interior cavity 54 bounded on one side by an interior surface of the body 48 and bounded on the other side by an interior surface of the cover 50. After the body 48 and cover 50 are assembled, the handpiece 12 has a smoothly contoured shape suitable for gripping and manipulation by an operator. The operator maneuvers the treatment tip 14 and treatment electrode 24 to a location proximate to the skin surface and, typically, to place the treatment electrode 24 in a contacting relationship with the skin surface.

The housing 46 includes a nose 56 and a window 58 in the nose 56 that is sized for the insertion and removal of the treatment tip 14. The electrical/fluid interface 52 is disposed between the window 58 and the interior cavity 54 enclosed inside the housing 46. The treatment tip 14 is sized to be inserted through the window 58 and configured to be physically engaged with the handpiece 12, as described below. In the engaged state, the contact pads carried on the substrate 30 of the treatment electrode 24 establish respective electrical connections with complementary electrical contacts 60 (FIG. 3), such as pogo pins, carried by the electrical/fluid interface 52 of the handpiece 12. These electrical contacts 60 are electrically coupled with one or more of the conductors 22 that extend from the handpiece 12 to the generator 26 and system controller 18. Treatment electrode 24 is at least partially exposed through the window 58.

The handpiece 12 may include a control panel 62 and a display 64 that may be carried by the cover 50. The control panel 62 may include various controls, such as controls 69, 70 used to respectively increase and reduce the treatment setting and controls 71, 72 that respectively enable and disable the controls 69, 70. The display 64 may be used to display information including, but not limited to, energy delivered, tissue impedance, duration, and feedback on procedure technique. The availability of the information displayed on the display 64 may conveniently eliminate the need to display identical information at the console 16 or may duplicate information displayed at the console 16. By displaying information at the handpiece 12, the operator can focus on the procedure without diverting his attention to glance at information displayed by the display on the console 16. In one embodiment, the display 64 may constitute a thin, flat liquid crystal display (LCD) comprised of a light source or reflector and an arbitrary number of color or monochrome pixels arrayed in front of the light source or reflector. A driver circuit (not shown) is provided to control the operation of the display 64.

The treatment tip 14 includes a rigid outer shell 66 and a nipple 34 that is coupled with the open rearward end of the outer shell 66 to surround an interior cavity. A fluid delivery member 41 is configured as a control valve to deliver a spray of a cryogen or similar coolant from a nozzle 39 onto the electrode 24. Extending rearwardly from a central fluid coupling member 32 is a conduit 45 having a lumen defining a fluid path that conveys a flow of the coolant to the nozzle 39. The coolant is pumped from a coolant supply (FIG. 6) through tubing that is mechanically coupled with a fitting 47 formed on the nipple 34 and hydraulically coupled with the lumen of the conduit 45.

The electrode 24 is exposed through a window 51 defined in a forward open end of the outer shell 66. The electrode 24 may be formed as a conductive feature on a substrate 30, which in a representative embodiment of the invention is a flexible sheet of dielectric material wrapped about a forward end of a support member 53. The rearward end of the support member 53 includes a flange 55 used to couple the support member 53 to the nipple 34. The flexible substrate 30 is wrapped or folded about the support member 53 such that the contact pads 57 are exposed through slots 59 defined in the nipple 34. A support arm 67 bridges the window 51 for lending mechanical support to the flexible substrate 30.

Figure 3:
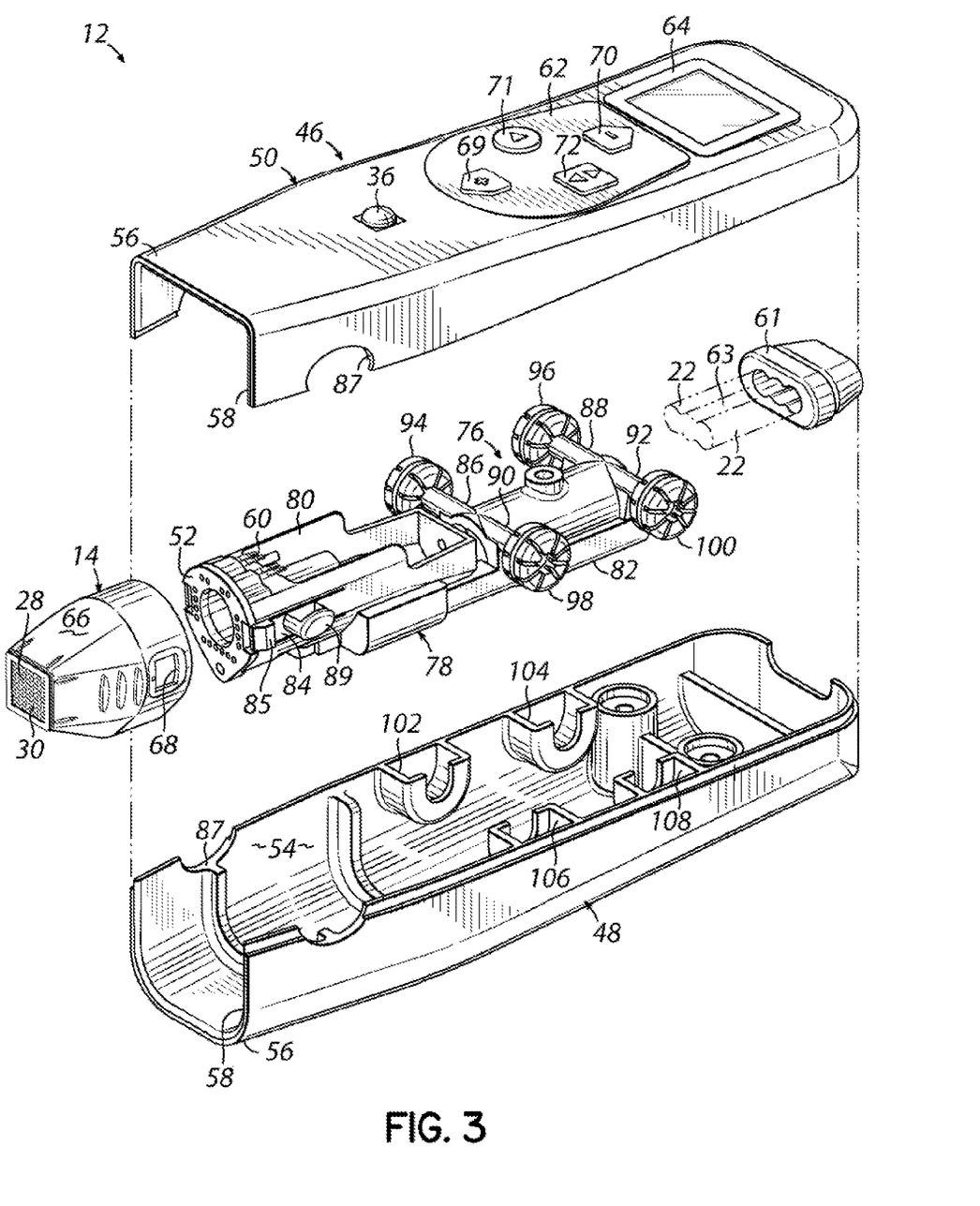
FIG. 3 is an exploded view of the assembly of FIG. 2.

The treatment tip 14 includes openings 68 defined on diametrically opposite sides of the outer shell 66. The openings 68 are used to temporarily secure the treatment tip 14 with the handpiece 12 in advance of a patient treatment procedure. A line 63 extends through the interior cavity 54 inside the housing 46 of handpiece 12. The line 63 is connected with the fluid delivery member 41 and the line 63 is further connected by a line 61 with the cryogen supply 65.

One purpose of the cryogen spray is to pre-cool the patient's epidermis, before powering the treatment electrode 24, by heat transfer between the treatment electrode 24 and the skin surface. The cooling creates a reverse thermal gradient in the tissue such that the temperature of the tissue at and near the skin surface is cooler than the temperature of the tissue deeper within the epidermis or dermis. As a result, the high frequency energy delivered to the tissue fails to heat all or a portion of the patient's epidermis to a temperature sufficient to cause significant epidermal thermal damage. Depths of tissue that are not significantly cooled by pre-cooling will warm up to therapeutic temperatures, which cause a desired therapeutic effect. The amount and/or duration of pre-cooling may be used to select the protected depth of untreated tissue. The cryogen delivered by the fluid delivery member 41 may also be used to cool portions of the tissue during and/or after heating by the high frequency energy transferred from the treatment electrode 24. Post-cooling may prevent or reduce heat delivered deeper into the tissue from conducting upward and heating shallower tissue regions, such as the epidermis, to temperatures which could thermally damage shallower tissue regions even though external energy delivery to the targeted tissue has ceased.

Various duty cycles of cooling and heating that rely on cooling and high frequency energy transfer from the treatment electrode 24 are utilized contingent upon the type of treatment and the desired type of therapeutic effect. The cooling and heating duty cycles may be controlled and coordinated by operation of the system controller 18 and fluid delivery member 41. Suitable cryogens include low boiling point fluids, but are not limited to, R134a (1,1,1,2-tetrafluoroethane) refrigerant, liquid nitrogen, HFO-1234ze (1,3,3,3-tetrafluoropropene) refrigerant, and R152a (1,1-difluoroethane) refrigerant. Heat can be extracted from the treatment electrode 24 by virtue of evaporative cooling of the cryogen, which lowers the temperature of the treatment electrode 24.

Figure 6:
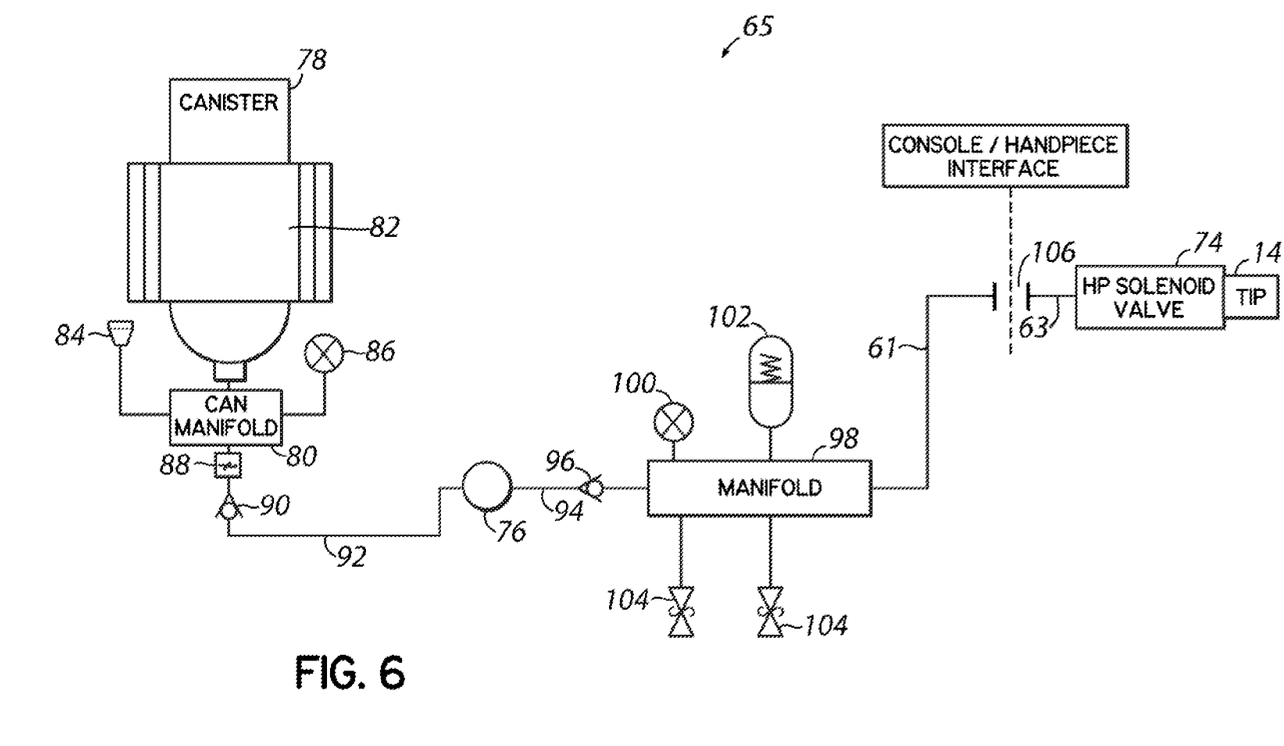
FIG. 6 is a schematic diagram of a cryogen supply system.

Referring now to FIG. 6, the cryogen supply 65 may include a pump 76, a manifold 80, a line 92 coupling the manifold 80 with the pump 76, a manifold 98, a line 94 coupling the manifold 98 with the pump 76, and a line 61 that extends from the console 16 to the handpiece 12. The pump 76 and manifolds 80, 98 may be housed at the console 16 of the treatment apparatus 10.

A canister 78 of cryogen is placed in fluid communication with the canister manifold 80 and is at least partially surrounded by a heater 82. The canister manifold 80 may include a muffler 84 and a pressure sensor 86 that are tapped into the internal fluid paths inside the manifold 80. The canisters 78 are prefilled with given volume of cryogen. When a canister 78 of cryogen is consumed and replaced with another canister 78 filled with cryogen, muffler 84 may function as an exhaust that allows the release of any residual pressure that might be present at or near the canister manifold 80. During operation of the cryogen supply 65, the canister 78 is heated to a selected temperature by heat energy transferred from the heater 82 to increase the internal pressure of the cryogen to a selected pressure or value. In some embodiments, the selected temperature is a temperature selected by a user that will result in an increase in the internal pressure of the cryogen and may vary depending upon the identity of the cryogen, as would be understood by a person having ordinary skill in the art. The system controller 18 may rely on pressure readings from the pressure sensor 86 as feedback in a closed-loop control system to control the operation of the heater 82 and thereby the internal pressure inside the canister 78. The temperature and pressure of the cryogen inside the canister 78 may be maintained at lower values than conventional because of the introduction of the pump 76 into the fluid path leading from the canister 78 to the handpiece 12. Conventionally, the heating of the cryogen in the canister 78 is used to increase fluid pressure of the cryogen in the canister 78 and thereby pressurizes the lines leading from the canister 78 to the handpiece 12. In contrast, because the pump 76 provides the primary source of fluid pressurization, the temperature of the cryogen in the canister 78 can be reduced to maintain a lowered pressure inside the canister 78 than conventional. The lowered temperature and pressure keeps the contained cryogen in a liquid state inside the canister 78 and the fluid line 92 leading to the pump 76 and prevents vapor development from cryogen vaporization.

Downstream from the canister manifold 80, a filter 88 in fluid line 92 may be used to remove contaminants that might be introduced upon replacing the cryogen canister 78. Contaminants may include human hair, skin, dust, dust mites, and other undesired material.

During replacement of the cryogen canister 78, the check valve 90 in fluid line 92 may be used to prevent the back flow of pressurized cryogen from downstream locations to the manifold 80 and loss through the muffler 84. During typical operation of the cryogen supply 65, the check valve 90 is moved to an open configuration by the fluid pressure of the cryogen in the portion of the line 92 between the check valve 90 and manifold 80; but during replacement of the cryogen canister 78, the check valve 90 moves to a closed position as the cryogen pressurization is absent. In this way, any cryogen contained in the cryogen supply 65 downstream of check valve 90 is confined and not lost.

The pump 76 may increase pressure of a liquid cryogen cooling system rapidly and precisely. By increasing or maintaining pressure of the liquid cryogen cooling system, the cryogen may remain in a liquid state until released to ambient conditions. The pump 76 operates to create a pressure differential between the line 92, which is at a comparatively low nominal pressure during operation, and the line 94, which is at a comparatively high nominal pressure during operation. In conventional cryogen supplies, all of the lines leading from the canister to the handpiece are maintained at the comparatively high pressure and none of these lines is maintained at the comparatively low pressure because, at least in part, the heating of the canister 78 provides pressurization of the cryogen. In an embodiment, the pump 76 may be a diaphragm pump. A diaphragm pump is a positive displacement pump that uses a combination of the reciprocating action of a diaphragm and suitable valves on either side of the diaphragm to pump the cryogen.

Typical pressures upstream of the liquid pump 76 may range from about 50 psi to about 80 psi, inclusive, or from about 60 psi to about 70 psi, inclusive, or about 61 psi, about 62 psi, about 63 psi, about 64 psi, about 65 psi, about 66 psi, about 67 psi, about 68 psi, about 69 psi, or any fractional part thereof. Typical pressures downstream of the liquid pump 76 may range from about 110 psi to about 130 psi, inclusive, or from about 115 psi to about 125 psi, inclusive, or about 116 psi, about 117 psi, about 118 psi, about 119 psi, about 120 psi, about 121 psi, about 122 psi, about 123 psi, about 124 psi, or any fractional part thereof. In alternative embodiments, typical pressures downstream of the liquid pump 76 may range from about 100 psi to about 130 psi, inclusive, or from about 105 psi to about 125 psi, inclusive, or about 106 psi, about 107 psi, about 108 psi, about 109 psi, about 110 psi, about 111 psi, about 112 psi, about 113 psi, about 114 psi, about 115 psi, about 116 psi, about 117 psi, about 118 psi, about 119 psi, about 120 psi, about 121 psi, about 122 psi, about 123 psi, about 124 psi, or any fractional part thereof. The pump 76 may provide instantaneous or near instantaneous pressurization of the lines 61, 94, which contrasts with the significant time delays that are experienced when relying on conventional heating of the cryogen canister to provide pressurization of the cryogen. The faster pressurization by the pump 76 may speed the performance of a patient treatment using the treatment apparatus 10. The pump 76 may also provide tighter control over the pressure in the lines 61, 94 such that the pressure is maintained in a narrower range than possible with conventional canister heating.

Optionally, a check valve 96 may be installed in the line 94 between the pump 76 and the manifold 98. The check valve 96 may prevent the pump 76 from experiencing a backpressure condition.

The manifold 98 may include a pressure sensor 100, an arrestor 102, and one or more relief valves 104. The arrestor 102 may function to minimize pressure surges that may be a byproduct of the operation of the pump 76. For instance, if the pump 76 is a diaphragm pump, reciprocating volume displacement may cause intermittent surge of cryogen with each expansion and contraction of the diaphragm and the arrestor 102 may dampen these intermittent surges. The relief valves 104 may be configured to open if the internal pressure in the manifold 98 exceeds some selected value, such as an unsafe maximum value.

As described above, the lines 61, 63 connect the manifold 98 to a control valve 74 providing the fluid delivery member 41, which is a component of the handpiece 12, through a fitting 106. The pressure in the line 63 is maintained at the elevated pressure present in the line 94. The fitting 106 may permit the handpiece 12 to be connected to the cryogen supply 65 and disconnected from the cryogen supply 65.

References herein to terms such as "vertical," "horizontal," etc. are made by way of example, and not by way of limitation, to establish a frame of reference. It is understood that various other frames of reference may be employed for describing the invention without departing from the spirit and scope of the invention. It is also understood that features of the invention are not necessarily shown to scale in the drawings. Furthermore, to the extent that the terms "composed of," "includes," "having," "has," "with," or variants thereof are used in either the detailed description or the claims, such terms are intended to be inclusive and open-ended in a manner similar to the term "comprising."

It will be understood that when an element is described as being "attached," "connected," or "coupled" to another element, it can be directly connected or coupled to the other element or intervening elements may be present. In contrast, when an element is described as being "directly attached," "directly connected," or "directly coupled" to another element, there are no intervening elements present.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

While the invention has been illustrated by a description of various embodiments and while these embodiments have been described in considerable detail, it is not the intention of the applicant to restrict or in any way limit the scope of the appended claims to such detail. Additional advantages and modifications will readily appear to those skilled in the art. Thus, the invention in its broader aspects is therefore not limited to the specific details, representative apparatus and method, and illustrative example shown and described. Accordingly, departures may be made from such details without departing from the spirit or scope of applicant's general inventive concept.

What is claimed is:

1. A method for treating tissue with electromagnetic energy, the method comprising:
   heating a fluid inside a container to a selected temperature that provides a pressurized fluid maintained in a liquid state inside the container; and
   pumping the pressurized fluid from the container to an energy delivery device configured to emit the electromagnetic energy.

2. The method of claim 1 wherein the pressurized fluid is pumped from the container to the energy delivery device using a diaphragm pump.

3. The method of claim 2 wherein the pressurized fluid is pumped from the container to the energy delivery device using a first line upstream of the diaphragm pump and a second line downstream of the diaphragm pump, the first line is at a first pressure, and the second line is at a second pressure.

4. The method of claim 3 wherein the first pressure is in a range from about 50 psi to about 80 psi, and the second pressure is in a range from about 110 psi to about 130 psi.

5. The method of claim 3 wherein the second pressure is greater than the first pressure.

6. The method of claim 1 wherein the pressurized fluid is pumped from the container to the energy delivery device using a diaphragm pump, the diaphragm pump is coupled to the container by a fluid line, and the pressurized fluid is also maintained under pressure in the liquid state inside the fluid line.

7. The method of claim 1 wherein the pressurized fluid is a coolant.

8. The method of claim 7 wherein the energy delivery device includes an electrode, and further comprising:
delivering a spray of the coolant from a nozzle to the electrode.

9. The method of claim 1 further comprising:
delivering the electromagnetic energy from the energy delivery device to treat the tissue.

10. An apparatus for treating tissue with electromagnetic energy, the apparatus comprising:
an energy delivery device configured to deliver the electromagnetic energy for treating the tissue, the energy delivery device including an electrode, a nozzle, and a control valve;
a first manifold configured to hold a container containing a fluid;
a heater configured to at least partially surround the container;
a cooling system including a pump configured to pump the fluid from the container to the energy delivery device; and
a second manifold arranged between the pump and the control valve, the second manifold including an arrestor configured to respond to pressure surges from operation of the pump,
wherein the pump is a diaphragm pump, and the control valve is configured to control delivery of the fluid from the nozzle to the electrode.

11. The apparatus of claim 10 further comprising:
a system controller communicatively coupled to the energy delivery device and to the cooling system, the system controller programmed to control operation of the heater to heat the fluid inside the container to a selected temperature that provides a pressurized fluid and to control the pump to pump the pressurized fluid from the container to the energy delivery device such that the fluid is maintained in a liquid state inside the container.

12. The apparatus of claim 10 wherein the energy delivery device is configured to emit the electromagnetic energy from the electrode.

13. The apparatus of claim 10 wherein the fluid is a coolant.

14. An apparatus for treating tissue with electromagnetic energy, the apparatus comprising:
an energy delivery device configured to deliver the electromagnetic energy for treating the tissue;
a first manifold configured to hold a container containing a fluid;
a heater configured to at least partially surround the container;
a cooling system including a pump configured to pump the fluid from the container to the energy delivery device;
a first fluid line coupling the first manifold with the pump;
a second manifold coupled to the first manifold by the first fluid line;
a second fluid line coupling the pump to the second manifold;
a first check valve in the first fluid line; and
a second check valve in the second fluid line.

15. The apparatus of claim 14 wherein the second manifold includes an arrestor configured to respond to pressure surges from operation of the pump.

16. The apparatus of claim 14 wherein the second manifold includes one or more relief valves.

17. The apparatus of claim 14 wherein the first manifold includes a pressure sensor, and the pressure sensor is tapped into a fluid path inside the first manifold.

18. The apparatus of claim 14 wherein the fluid is a coolant.

19. The apparatus of claim 14 wherein the pump is a diaphragm pump.

* * * * *